United States Patent [19]

Sujeeth

[11] Patent Number: 5,637,733
[45] Date of Patent: Jun. 10, 1997

[54] SYNTHESES OF FLUORESCEIN COMPOUNDS WITH EXCESS RESORCINOL AS A SOLVENT

[75] Inventor: Puthalath K. Sujeeth, Maryland Heights, Mo.

[73] Assignee: Warner-Jenkinson Company, Inc., St. Louis, Mo.

[21] Appl. No.: 534,285

[22] Filed: Sep. 27, 1995

[51] Int. Cl.$^6$ ................................. C07D 311/82
[52] U.S. Cl. ............................................ 549/223
[58] Field of Search ............................... 549/223

[56] References Cited

U.S. PATENT DOCUMENTS

| | | | |
|---|---|---|---|
| 1,931,049 | 10/1933 | Woods et al. | 260/65 |
| 1,965,842 | 7/1934 | Kranz | 260/62 |
| 2,355,359 | 8/1944 | Bainbridge et al. | 8/6 |
| 2,980,696 | 4/1961 | Körbl | 260/327 |
| 4,933,471 | 6/1990 | Lee | 549/33 |
| 5,066,580 | 11/1991 | Lee | 435/721 |

FOREIGN PATENT DOCUMENTS

| | | | |
|---|---|---|---|
| 141962A1 | 5/1985 | European Pat. Off. | C07D 491/107 |
| 468821A1 | 1/1992 | European Pat. Off. | C07D 311/82 |

OTHER PUBLICATIONS

Khanna, PL et al CA 95:38669 (1981).

On The Theory of Indicators and the Reactions of Phthaleins and their Salts, S.F. Acree and E. Slagle, JACS, 1909, 37, pp. 115–147.

Organic Reactions with Boron Fluoride, J.F. McKenna and F.J. Sowa, JACS, 1938, 60, pp. 124–125.

Detection and Determination of Starting Materials and Uncombined Intermediates of Organic Synthesis as well as Subsidiary Dyes Remaining in Cosmetic Coal–Tar Dyes by High Performance Liquid Chromatography (II), Y. Ito, et al., J. Soc. Cosmet. Chem. Japan, 1983.

Complementary Use if Counter–Current Chromatography and Preparative Reversed–Phase High–Performance Liquid Chromatography in the Separation of a Synthetic Mixture of Brominated Tetrachlorofluoresceins, A. Weiss, et al., *Journal of Chromatography*, 607 (1992), pp. 47–53.

Fluorescein and Some of its Derivatives, W.R. Orndorff and A.J. Hemmer, JACS, 1927, 49, pp. 1272–1280.

2,4–Dihydroxybenzoyltetrachloro–o–Benzoic Acid and 2,3,4–Trichloro–6–Hydroxyxanthone–1–Carboxylic Acid and Some of their Derivatives, W.R. Orndorff and W.A. Adamson, JACS, 1918, 40, pp. 1235–1237.

Tetrachlorofluorescein and Some of its Derivatives, W.R. Orndorff and E.F. Hitch, JACS, 1914, 36, pp. 680–725.

*Primary Examiner*—Amelia Owens
*Attorney, Agent, or Firm*—Whyte Hirschboeck Dudek S.C.

[57] ABSTRACT

A process for the manufacture of fluorescein compounds suitable for conversion to FDA certified dyes is described. The fluorescein compounds, and in particular fluorescein (also known as Solvent Yellow 94 or D&C Yellow No.7) and 3,4,5,6-tetrachlorofluorescein, are made by a process involving the condensation of a phthalic anhydride with several molar excess of a resorcinol, the resorcinol being employed not only as a reactant, but also as a solvent for the reaction. This process also can employ the unreacted resorcinol and any intermediates or by-products from the condensation reaction as a reactant and as a solvent in subsequent condensation reactions.

9 Claims, No Drawings

SYNTHESES OF FLUORESCEIN COMPOUNDS WITH EXCESS RESORCINOL AS A SOLVENT

BACKGROUND OF THE INVENTION

1. Field of the Invention

This invention relates to a process for the manufacture of fluorescein compounds, in particular fluorescein (also known as Solvent Yellow 94 or D&C Yellow No.7) and 3,4,5,6-tetrachlorofluorescein. In one aspect, the invention relates to the manufacture of a fluorescein compound by condensing phthalic anhydride with an excess of resorcinol, the resorcinol being employed both as a reactant and as a solvent for the reaction. In another aspect, the invention relates to the use of recycled resorcinol as a reactant and as a solvent for the reaction.

2. Description of the Prior Art

The production of fluorescein compounds is well known in the art, and it involves generally the condensation of phthalic anhydride with resorcinol in the presence or absence of a condensing agent. Fluorescein was originally prepared by Baeyer by fusing suitable proportions of phthalic anhydride and resorcinol (Baeyer,*Ber.*,4,555, (1871)and *Ann.*,183,1–74, (1876). During the early twentieth century, Orndorff et.al. studied this process in considerable detail (Orndorff et.al. *JACS*, 36,680–725,(1914); *JACS*, 40,1235–57,(1918); and *JACS*, 49,1272–80(1927)), and concluded that the preparation of fluorescein compounds in higher and purer yields requires the use of a condensing agent such as zinc chloride, phosphorus pentoxide etc. (Orndorff and Hitch,*JACS*, 36,684–86,(1914)).

Improvements to the fluorescein preparation process that obviated the formation of a final hard, infusible mass and avoided local overheating and resultant production of by-products (low yield and purity) were disclosed in U.S. Pat. No. 1,931,049 to Woods, et al. and U.S. Pat. No. 1,965,842 to Kranz. The improvements involve the use of inert organic liquids as the solvent for the reaction mixture. Products prepared in this manner, however, are contaminated by new impurities. As such, the contaminants require essentially complete removal before the products can be used as FDA certified dyes or dye intermediates.

SUMMARY OF INVENTION

According to this invention, fluorescein compounds suitable for conversion to FDA certified dyes are made by a process involving the condensation of a phthalic anhydride with several molar excess of a resorcinol, the resorcinol being employed not only as a reactant, but also as a solvent for the reaction. In one embodiment of this invention, the unreacted resorcinol and any intermediates or by-products from the condensation reaction are recycled back to the process for use again both as a reactant and as a solvent.

This invention offers several advantages over other known methods of manufacturing fluorescein compounds, in particular fluorescein (also known as Solvent Yellow 94 or D&C Yellow No.7) and 3,4,5,6-tetrachlorofluorescein. First, by employing resorcinol as both a reactant and a solvent, the present process eliminates the opportunity for contamination of the final product by impurities that result from the use of a condensing agent and that later require removal. Second, the capture and reuse of unreacted resorcinol and any reaction intermediates and/or by-products in subsequent reactions eliminates the need for disposal of these materials. As such, the cost associated with the manufacture of fluorescein compounds is greatly reduced.

DETAILED DESCRIPTION OF INVENTION

The fluorescein compounds of this invention are of structural formula I:

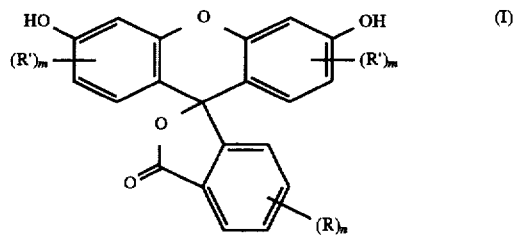

in which each R and R' is independently halogen or an aliphatic, alicyclic, aryl or an inertly-substituted aliphatic, alicyclic or aryl group, n is an integer of 0–4 and m is an integer of 0–3. The preferred halogen is chlorine. When n and m are 0, formula I represents fluorescein. When m is 0n, is four and R is chlorine, formula I represents 3,4,5,6-tetrachlorofluorescein. As here used, "inertly-substituted" means those substituents that for all intent and purposes are essentially nonreactive with the starting materials and products of the process at process conditions.

These fluorescein compounds are prepared by condensing a phthalic anhydride compound with several molar excess of resorcinol or recycled resorcinol, the resorcinol being employed both as a reactant and as a solvent. The phthalic anhydride compounds of this invention are of structural formula II:

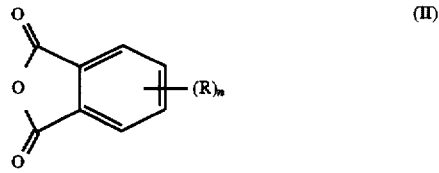

in which R and n are as previously defined. When n is 0, formula II represents phthalic anhydride. As here used, "phthalic anhydride," includes phthalic anhydride of any grade. Moreover, since phthalic acid is a hydrated equivalent of phthalic anhydride and can be employed instead of the anhydride (Orndorff and Hitch, *JACS*, 36, 685, (1914), "phthalic anhydride" as here used also includes phthalic acid. Tetrachlorophthalic anhydride (n is 4 and each R is a Cl group) is a representative inertly-substituted phthalic anhydride. The resorcinol compounds of this invention are of structural formula III:

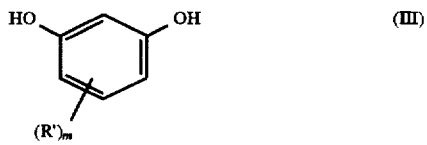

in which R' and m are as previously defined with the proviso that at least one of the 4 and 6 positions of the resorcinol ring is not occupied by a R' group. When m is 0, formula III represents resorcinol. As here used, "resorcinol," includes resorcinol of any grade. As here used "recycled resorcinol," means unreacted resorcinol and any intermediates (e.g. dihydroxybenzoylbenzoic acid) and/or by-products that are present at the end of the condensation reaction between a phthalic anhydride and a resorcinol compound and which are recovered, recycled and used as the reactant/solvent in subsequent condensation reactions.

In the condensation reaction involving a phthalic anhydride and resorcinol compound and/or recycled resorcinol, the resorcinol and/or recycled resorcinol is used in several molar excess relative to phthalic anhydride. The maximum excess is a factor based on economy and convenience. Typically, however, the maximum excess does not exceed 5, preferably it does not exceed 3.

The fluorescein compounds of this invention can be used directly in drug and cosmetic applications or indirectly as intermediates for the preparation of FDA certified dyes (including food dyes e.g. FD&C Red No.3). Fluorescein compounds used in these types of applications require FDA approval which is dependent on, among other things, product purity. For all intent and purposes, product purity is best controlled through batchwise purification. The process, however, may be adapted so as to be carried out continuously. The reaction pressure of this process is not critical to the invention and will vary depending on, among other things, the reactants and equipment. Preferably, however, the process is operated at atmospheric pressure or at a slightly reduced pressure. One of the advantages of this process is that it does not require dedicated equipment and thus on an industrial scale, the process can be conducted in multi-purpose equipment such as conventional closed reactors capable of operation at high temperatures.

The reaction temperature of this process is not critical to the invention, and can vary to convenience and will depend on, among other things, the reactants and equipment. Typically, the reaction mixture or mass is heated to a temperature of at least about 175 C., preferably at least about 185 C. The maximum temperature, however, generally does not exceed 225 C., preferably it does not exceed 210 C. If water is associated with any of the reactants, the time required to complete the condensation of phthalic anhydride and resorcinol is generally longer than if the reactants were anhydrous. Depending upon the amount of water in the reactants, the time required to complete the condensation varies from about 2 to 20 hours. For example, a reaction which uses dry reactants generally requires about 2 hours for completion. Recycled resorcinol, however, typically contains from about 65% to 80% water and as such, can require from about 10 to 20 hours to remove the water from the reaction mixture.

Although not required upon completion of the condensation, the temperature of the reaction mixture is typically lowered by about 25 C. before the reaction mixture is quenched into a specific amount of water to form a slurry. The amount of water will vary depending on, among other things, the reactants and equipment. However, there should be sufficient water to quench the reaction mixture so as to obtain a maximum amount of solid fluorescein compounds while keeping the reaction intermediates and by-products in solution.

The fluorescein compound precipitates in the water quench, and it is then recovered by filtration. The fluorescein product is washed with hot water to remove adhering unreacted resorcinol and process intermediates (e.g. dihydroxybenzoylbenzoic acid) and by-products of the condensation reaction. The filtrate from the above reaction is recycled for use in subsequent condensation reactions.

The process of this invention typically produces yields of fluorescein compounds in excess of 90% and is substantially free of reactants (i.e., the compounds are at least about 85% pure, preferably at least about 87% pure and still more preferably at least about 90% pure). Furthermore, the process reduces product waste by recovering and recycling the unreacted reactants or resulting by-products. The process also avoids contamination of the final product by solvent impurities which would result from the use of an inert solvent, e.g. ortho dichlorobenzene. Purity is based, at least in substantial part, on the efficacy of the purification process. If materials of higher purity are required, this can be accomplished by conventional methods e.g. dissolve in base, treat with activated carbon, filter and precipitate with acid, or dissolve the soluble impurities in solvents such as n-butanol, DMF etc.).

The invention is further described by the following Examples. Unless otherwise indicated, all parts and percentages are by weight.

SPECIFIC EMBODIMENTS

EXAMPLE 1

Resorcinol (470 g, technical grade 99.4%, white flakes) was added to a one-liter jacketed glass vessel and heated to 135 C. in order to melt the resorcinol. Once melted, phthalic anhydride (124 g, technical grade 99.7%, white flakes) was added to the vessel, and the reaction mixture was blanketed with nitrogen, mixed and heated to 200 C. The reaction mixture was held at 200–215 C. for approximately 2 hours while the water (24 g) was removed by distillation. Upon completion, the reaction mixture was cooled to 185 C. and quenched with water by transferring the reaction mixture under nitrogen to a stirred vessel containing water (approximately 500 ml). The vessel was then rinsed with water to transfer all of the precipitated product. The combined product slurry in water was digested at 75 C. (to dissolve any unreacted intermediates) and cooled to 35 C. The product was recovered by vacuum filtration in the form of a filter cake. This filter cake was washed free of dissolved impurities, such as resorcinol, by mixing and heating with fresh water (approximately 1L), filtering and rinsing with about 800 ml boiling hot water. This cake upon drying yielded fluorescein (250.1 g).

The composition of the product stream was analyzed using High Pressure Liquid Chromatography (HPLC), and the fluorescein compound had a purity of 90.4%.

EXAMPLE 2

The filtration mother liquor generated in Example 1 was added to a one-liter jacketed glass vessel, blanketed with nitrogen and heated to 135 C. to remove the water. Once the water was removed and the reactor temperature reached 135 C., fresh resorcinol (210 g, technical grade 99.4%, white flakes) was added to the vessel. Phthalic anhydride (124 g, technical grade 99.7%, white flakes) was added to the melted resorcinol, and the reaction mixture was blanketed with nitrogen, mixed and heated to 200 C. The reaction mixture was held between 200 and 210 C. for approximately four hours while the water (378 g) was removed by distillation. Upon completion, the reaction mixture was cooled to 185 C. and quenched with water by transferring the reaction mixture under nitrogen to a stirred vessel containing water (approximately 500 ml). The vessel was rinsed with water to transfer all of the precipitated product. The combined product slurry in water was digested at 75 C. and cooled to 35 C. The product was recovered by vacuum filtration in the form of a filter cake. This filter cake was washed free of dissolved impurities by mixing and heating with fresh water (approximately 800 ml), filtering and rinsing with about 700 ml boiling hot water. This cake upon drying yielded fluorescein (315.6 g).

The composition of the product stream was analyzed using HPLC, and the fluorescein compound had a purity of 87.1%.

EXAMPLE 3

A one-liter jacketed glass vessel was charged with filtration mother liquor and blanketed with nitrogen. Water (604 g) was distilled off by heating the jacket to 130 C. and holding at 130 C. for 3.5 hours. After the water was removed, resorcinol (250 g, technical grade 99.495, white flakes) was added to the vessel. Once the resorcinol was melted, tetrachlorophthalic anhydride (242 g TETRATHAL™, technical grade 98.5%, white flakes) was added. The reaction mixture was then mixed and heated to 200 C., and then held at 200–215 C. for approximately 2 hours while the water (50 g) was removed by distillation. Upon completion, the reaction mixture was cooled to 185 C. and quenched with water by transferring the reaction mixture under nitrogen pressure to a stirred vessel containing water (approximately 500 ml). The reaction vessel was rinsed with water to transfer all of the precipitated product. The combined product slurry in water was digested at 75 C. and cooled to 35 C. The product was then recovered by vacuum filtration. The filter cake was rinsed with small amount of hot water (<50 ml), combined this rinse with mother liquor and was recycled as is to the next batch. The filter cake was suspended in hot water (400 ml) and refiltered. The cake was washed with 600 ml of hot water and then dried. The dried cake yielded 3,4,5,6-tetrachlorofluorescein (267 g).

The tetrachlorofluorescein was analyzed using HPLC, and had a purity of approximately 91.1%.

What is claimed is:

1. A process for the preparation of a fluorescein compound, the process comprising the steps of:

(A) condensing a neat reaction mixture of a phthalic anhydride compound and a several molar excess amount of a resorcinol compound to form the fluorescein compound;

(B) quenching the reaction mixture of step (A) with water; and (C) recovering the fluorescein compound from the quench of step (B).

2. The process of claim 1, further comprising the step of:

(D) recycling the reaction mixture obtained from step (C) for use as the resorcinol in the condensation reaction of step (A).

3. The process of claim 1 wherein the fluorescein compound has the formula:

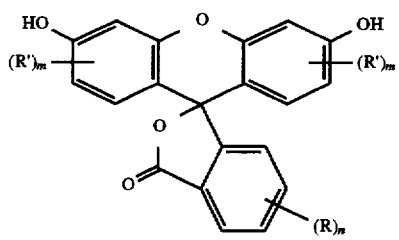

in which each R and R' is independently halogen or an aliphatic, alicyclic, aryl or an inertly-substituted aliphatic, alicyclic or aryl group;

n is an integer of 0–4; and m is an integer of 0–3;

the phthalic anhydride has the formula:

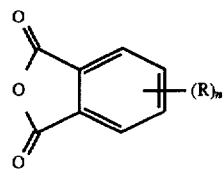

in which R is independently halogen or an aliphatic, alicyclic, aryl or an inertly-substituted aliphatic, alicyclic or aryl group; and n is an integer of 0–4; and the resorcinol has the formula:

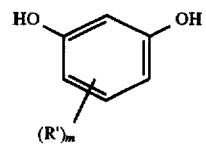

in which R' is independently halogen or an aliphatic, alicyclic, aryl or an inertly-substituted aliphatic, alicyclic or aryl group; and m is an integer of 0–3.

4. The process of claim 1 wherein the reaction mixture is condensed at a temperature from between about 185 C. to about 215 C.

5. The process of claim 1 wherein up to about 5 moles of the resorcinol is used per mole of phthalic anhydride.

6. A process for the preparation of fluorescein, the process comprising the steps of:

(A) condensing a neat reaction mixture of about one mole of phthalic anhydride compound and up to about 5 moles of a resorcinol compound at temperature from about 185 C. to about 215 C.;

(B) quenching the reaction mixture with water; and (C) isolating the fluorescein from the reaction mixture.

7. The process of claim 6, further comprising the step of:

(D) recycling the reaction mixture obtained from step (C) for use as the resorcinol in the condensation reaction of step (A).

8. A process for the preparation of tetrachlorofluorescein comprising the steps of:

(A) condensing a neat reaction mixture of about one mole of a tetrachlorophthalic anhydride compound and about 5 moles of a resorcinol compound at a temperature from about 185 C. to about 215 C.;

(B) quenching the reaction mixture with water; and (C) isolating the tetrachlorofluorescein from the reaction mixture.

9. The process of claim 8, further comprising the step of:

(D) recycling the reaction mixture obtained from step (C) for use as the resorcinol in the condensation reaction of step (A).

* * * * *

UNITED STATES PATENT AND TRADEMARK OFFICE
CERTIFICATE OF CORRECTION

PATENT NO. : 5,637,733

DATED : June 10, 1997

INVENTOR(S) : Puthalath K. Sujeeth

It is certified that error appears in the above-indentified patent and that said Letters Patent is hereby corrected as shown below:

Column 2, line 21, insert --,-- between "0" and "n"

Coloumn 3, line 34, "If" begins a new paragraph

IN THE CLAIMS:

Column 5, line 11, delete "99.495" and substitute therefor --99.4%--

Column 6, line 41, insert --a-- between "at" and "temperature"

Signed and Sealed this

Sixteenth Day of September, 1997

Attest:

BRUCE LEHMAN

Attesting Officer

Commissioner of Patents and Trademarks